(12) United States Patent
Hoarau et al.

(10) Patent No.: US 7,354,402 B2
(45) Date of Patent: Apr. 8, 2008

(54) INTRAORAL DATA INPUT TOOL

(76) Inventors: Yves R. Hoarau, 250 Reservation Rd., Suite H, Marina, CA (US) 93933; Eric Hoarau, 250 Reservation Rd., Suite H, Marina, CA (US) 93933

( * ) Notice: Subject to any disclaimer, the term of this patent is extended or adjusted under 35 U.S.C. 154(b) by 0 days.

(21) Appl. No.: 10/817,055

(22) Filed: Apr. 2, 2004

(65) Prior Publication Data
US 2005/0221252 A1    Oct. 6, 2005

(51) Int. Cl.
*A61B 8/00*    (2006.01)
*A61C 3/00*    (2006.01)

(52) U.S. Cl. .......................... 600/443; 433/31
(58) Field of Classification Search ............. 600/443, 600/459, 437, 447, 441; 73/625, 626, 618
See application file for complete search history.

(56) References Cited

U.S. PATENT DOCUMENTS

| | | | |
|---|---|---|---|
| 4,791,940 A | 12/1988 | Hirschfeld et al. | |
| 4,995,403 A | 2/1991 | Beckman et al. | |
| 5,022,856 A | 6/1991 | Zimble | |
| D320,075 S | 9/1991 | Berlin | |
| 5,100,318 A | 3/1992 | Demyun et al. | |
| 5,144,753 A | 9/1992 | Murphy | |
| 5,303,148 A * | 4/1994 | Mattson et al. | 600/437 |
| 5,318,442 A | 6/1994 | Jeffcoat et al. | |
| 5,460,522 A | 10/1995 | Scarffe | |
| 5,752,827 A | 5/1998 | Baron et al. | |
| 5,882,195 A | 3/1999 | Low et al. | |
| 5,897,509 A | 4/1999 | Toda et al. | |
| 5,993,209 A | 11/1999 | Matoba et al. | |
| 6,276,934 B1 | 8/2001 | Rakocz | |
| 6,443,729 B1 | 9/2002 | Watson | |
| 6,544,036 B1 | 4/2003 | Brattesani | |
| 6,575,908 B2 * | 6/2003 | Barnes et al. | 600/443 |
| 2002/0133096 A1 | 9/2002 | Toda et al. | |
| 2003/0156283 A1 * | 8/2003 | Jung et al. | 356/326 |

FOREIGN PATENT DOCUMENTS

| | | |
|---|---|---|
| EP | 0 296 520 A2 | 12/1988 |
| EP | 0 296 520 A3 | 11/1989 |
| EP | 0 572 387 B1 | 8/1996 |

\* cited by examiner

*Primary Examiner*—Cris Rodriguez
*Assistant Examiner*—Candice C Stokes

(57) ABSTRACT

An intraoral data input tool for use during dental examination of a patient comprises a discoid head attached to a handle. The discoid head includes a data input device which is responsive to force applied by a stylus, and may also include a mirror. The input device may be a set of push buttons or a touch sensitive display. The intraoral input device is configured to allow a dental examiner to input data while the input device is positioned in the patient's mouth. The data input device is linked to a computer system either by an electrical connector and cable or a wireless communication device. A display may be included in the discoid head; the display may be used for confirmation of input examination data.

40 Claims, 7 Drawing Sheets

INTRAORAL DATA INPUT TOOL

BACKGROUND OF THE INVENTION

1. Field of the Invention

The invention relates generally to the field of dental instruments and more particularly to dental data input tools.

2. Description of the Related Art

A dental examination, such as a periodontal examination or charting, involves collecting a large amount of data from a patient. For example, a periodontal probing procedure will typically require the dentist or hygienist to take and record six measurements per tooth. Furthermore, a periodontal examination may include probing, measurement of tooth mobility and furcation, and observation of bleeding and suppuration; the type of data to be recorded is sufficiently complex to require a sophisticated input device, such as a computer keyboard or finger keypad. Various software programs are available to streamline the process of collecting dental examination data.

A dental assistant can help in the dental data collection process by recording data called out by the dentist or hygienist as the examination is conducted. However, there is a need for an efficient means of data input by the dentist or hygienist without requiring a dental assistant.

The dentist or hygienist can input data as the dental examination proceeds by using a keyboard or finger keypad, placed in a convenient position. U.S. Pat. No. 5,752,827 to Baron et al. describes a periodontal examination apparatus which includes a finger keypad with a display. In one embodiment the finger keypad is described as being mounted on the forearm of the dentist or hygienist; consequently, the dentist or hygienist can probe and enter data without setting the probe down or moving positions. However, the use of such keyboards or finger keypads requires the dentist or hygienist to divert his/her attention from the patient's mouth and to change his/her visual focus to the input device and associated display; considering the large number of times data is recorded during a typical periodontal examination, eye fatigue can become an issue for the dentist or hygienist. There is a need for a more ergonomic method of data input which allows the dentist or hygienist to maintain their visual focus on the patient's mouth, thereby reducing eye fatigue.

SUMMARY OF THE INVENTION

The present invention provides an apparatus and method for data input during dental examination of a patient. The data input tool is configured to allow ease of data input by a dental examiner when the tool is positioned in or near the patient's mouth. The intraoral data input tool includes a handle and a head attached to one end of the handle. The head includes a data input device which is operable by a stylus. The data input device can be a multiplicity of push buttons and/or a touch sensitive display. In preferred embodiments of the tool, the head is discoid. Further, the head can include a display, other than a touch sensitive display. Furthermore, the head can also include a mirror. The stylus can conveniently be a dental probe. The data input tool can be linked to a controller by either an electrical cable or a wireless communication device. The controller has an operating program that can include routines for periodontal examination and dental charting. Peripheral devices such as a display, a keyboard, a voice synthesizer and an auxiliary input device can be electrically connected to the controller.

Another embodiment of the invention is a method for dental data collection including: examining a patient's tooth; during the examination, inputting data relating to this tooth on an intraoral data input tool, where the data input tool is positioned at least partially within the patient's mouth. A dental examiner repeats these steps for each of the patient's teeth desired to be examined until all desired data is input. The data is input by the dental examiner using a stylus to activate: at least one of a multiplicity of push buttons included in the data input tool; and/or a touch sensitive display included in the data input tool. The input data can be confirmed by: viewing the data on a display included in the intraoral data input tool; and/or listening to a computer synthesized recitation of the data. When periodontal data is collected, the above method is followed except it is the patient's tooth and related tissues that is examined and for which data is input on the intraoral data input tool.

DETAILED DESCRIPTION

Figure 1:
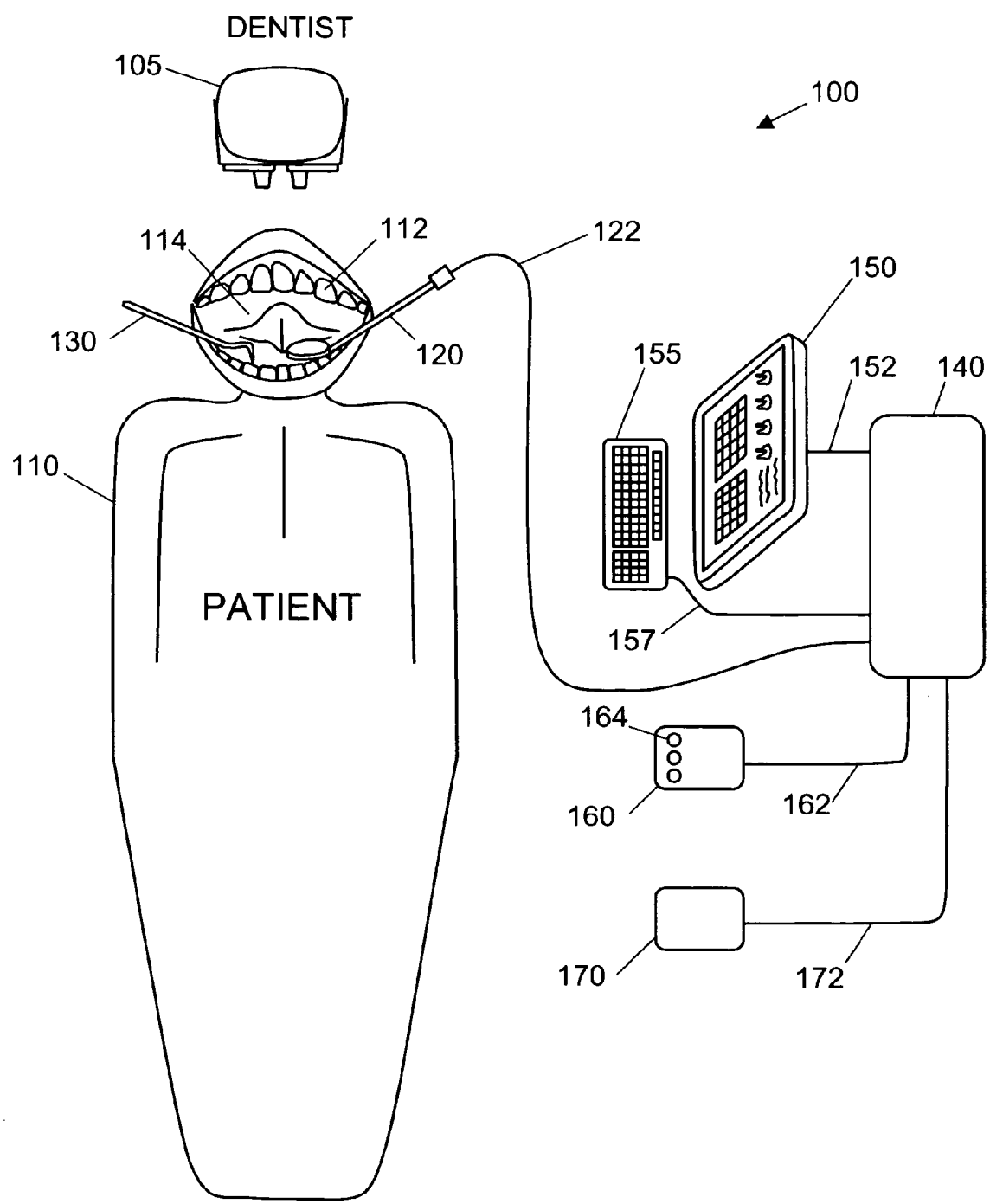
FIG. 1 is a top view schematic representation of a first embodiment of a dental data input system in accordance with the invention.

With reference to FIG. 1, a top view of a first embodiment of a dental data input system 100 is shown with a dentist 105 positioned behind a reclined patient 110; the dentist is in the process of acquiring dental examination data. Note that considering the relative position of the dentist and the patient, a mirror is needed in order to properly examine the patient's upper teeth. A dental probe 130 is shown positioned in the patient's mouth 114 for examination of patient's teeth 112 and surrounding tissues. An intraoral data input tool 120 is also positioned in the patient's mouth; in preferred embodiments the intraoral data input tool includes a mirror. The dentist holds the probe in one hand and the intraoral data input tool, by its handle, in the other hand; the dentist's hands are not shown in the figure so as to clearly show the probe and intraoral data input tool. The intraoral data input tool includes a data input device situated on the head of the tool (see FIG. 2). The dentist or hygienist can use the dental probe 130 to input data on the intraoral data input tool 120 during a dental examination of the patient. This data input can be done with the data input tool positioned partially within the patient's mouth; consequently, the dentist or hygienist can maintain his/her visual focus on the patient's mouth during data input. The intraoral data input tool must have an ergonomic design, suitable for use by the dentist or hygienist within, or partially within, the patient's mouth. For example: the handle of the data input tool should be designed to resist unwanted rotation of the head, particularly when inputting data; the data input tool should have a handle design that the dentist or hygienist can grip with minimal resultant hand fatigue; and the head of the data input tool should be designed to be comfortable for the patient during use. In preferred embodiments, the intraoral data input tool is similar in size and shape to a standard dental mirror—a discoid head approximately 2.5 cm, or less, in diameter with a handle approximately 13 cm, or less, long.

For many dental examinations the collection of dental data is done on a tooth by tooth basis. For example, the dentist or hygienist can use the following steps: (1) examining a tooth; (2) during the examining step, inputting data for this tooth on an intraoral data input tool, while the tool is positioned partially within the patient's mouth; and (3) repeating the examining and inputting steps for each of the patient's teeth desired to be examined, until all desired data is input. Clearly, in the case of a periodontal examination these steps will apply for a tooth and related tissues. Note that the above steps will apply when the dentist or hygienist examines only a few of the patient's teeth—for example, when measuring tooth mobility—and also when the dentist or hygienist examines all of the patient's teeth (and surrounding tissues)—for example, when conducting periodontal probing. Furthermore, the above steps will apply when the dentist or hygienist examines most teeth (and surrounding tissues) twice. For example, periodontal probing typically proceeds by taking measurements for all buccal sides of the upper teeth (starting with the rear molar on one side and progressing toward the rear molar on the other side), then for all lingual sides of the upper teeth (starting with the rear molar for which the last buccal measurements were taken and progressing back to the other rear molar), then for all buccal sides of the lower teeth and finally for all lingual sides of the lower teeth, requiring that most teeth are visited twice. Precisely when data is input during the examining step will depend on the type of dental examination and the individual dentist or hygienist. Data may be input after each individual measurement or observation—a typical procedure when measuring tooth mobility. Alternatively, when multiple measurements are taken for a tooth, all or some of the data from these measurements may be input after completing all or some of the measurements. For example, during a periodontal probing routine the dentist or hygienist will typically take three measurements for one tooth, and then input the three values together before moving on to the next tooth. Furthermore, a dentist or hygienist with a good memory may choose to enter multiple measurements for multiple teeth at the same time. For example, during a periodontal probing routine the dentist or hygienist may take six measurements (three measurements for each of two teeth), and then input the six values together.

In FIG. 1, the intraoral data input tool 120 is connected to a controller 140 by electrical cable 122. Alternatively, the intraoral data input tool can be linked to the controller by wireless communication—the intraoral data input tool can contain a wireless communication device (see FIG. 7). In preferred embodiments the controller 140 is a personal computer. Display 150, keyboard 155, auxiliary input device 160 and voice synthesizer 170 are also connected to the controller by electrical cables 152, 157, 162 and 172, respectively. The auxiliary input device 160 has keys 164; these keys can be operated by finger, stylus, or other convenient tool. Alternatively, the keys can be replaced by pressure pads, thus providing an auxiliary input device which is easier to clean. Furthermore, the auxiliary input device is positioned within reach of the dentist or hygienist, so that he/she can enter data on the auxiliary input device without moving positions. The voice synthesizer 170 can be used to generate: call outs of required data inputs; and recitations of input examination data for confirmation purposes. The voice synthesizer is shown as being separate from the controller; however, in other embodiments of the dental data input system it can be integrated into the controller.

The controller includes an operating program which includes one or more of the following dental routines: periodontal examination and dental charting. Where periodontal examination can include probing, measurement of tooth mobility and furcation, and observation of bleeding and suppuration, and charting can be historic, diagnostic and treatment. A dental routine can be selected using the keyboard 155; furthermore, some embodiments of the intraoral data input tool and the auxiliary input device are configured to allow selection of a dental routine—for example see FIGS. 9 & 10.

Figure 2:
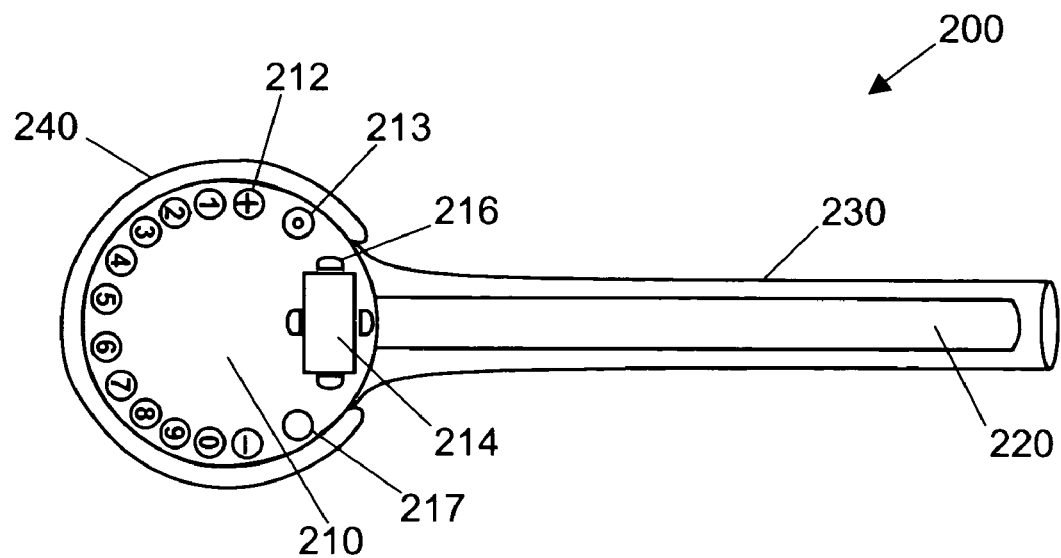
FIG. 2 is a top view of a first embodiment of an intraoral data input tool with a disposable translucent cover in accordance with the invention.
Figure 3:
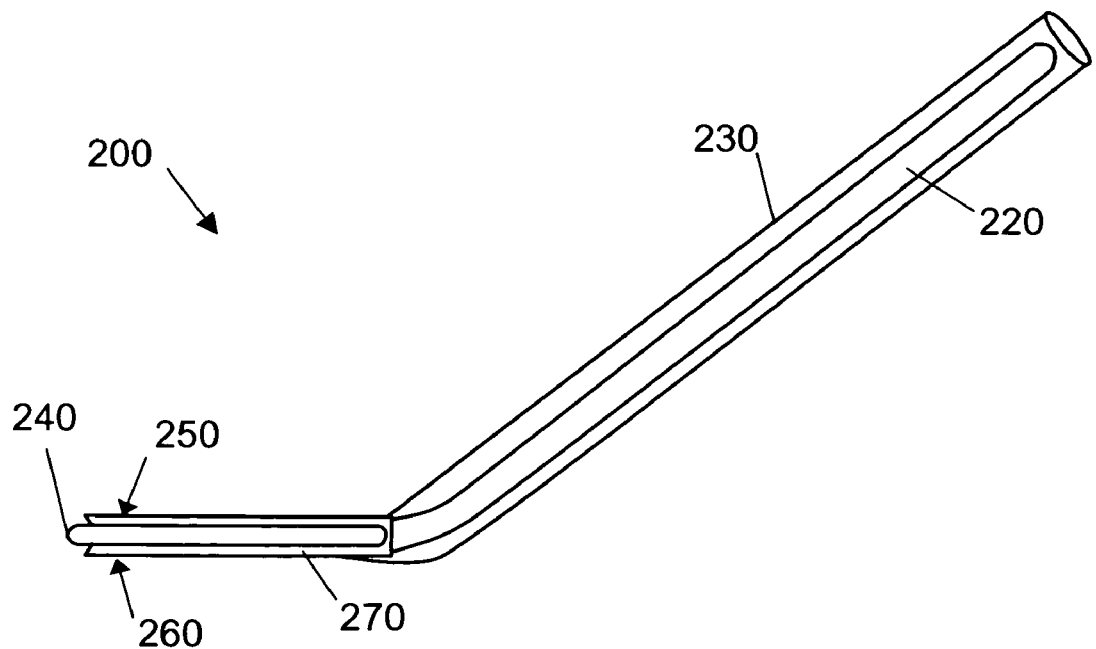
FIG. 3 is a side view of the intraoral data input tool of FIG. 2.

With reference to FIGS. 2 & 3, two views of a first embodiment of an intraoral data input tool 200 are shown. The intraoral data input tool has a head 210 attached to a handle 220. The head has a top flat surface 250, bottom flat surface 260 and a side surface 270; the side surface is concavely shaped so as to fit a clamp 240. The head is discoid and the clamp is a c-clamp. The clamp is designed to hold a translucent disposable cover 230 in place—the disposable cover is held conformal with the top surface of the head to ensure that the features on the top surface are clearly visible. The disposable cover is required for hygiene, when the intraoral data input tool is not a single use disposable item. The top surface 250 of the head 210 is shown with a set of twelve data push buttons 212, an "enter" push button 213, a display 214, a set of four location identifying push buttons 216 surrounding the display and an 'erase' push button 217. This top surface configuration is for a periodontal tool. The push buttons can be pressure pads or another type of pressure activated switch; the push buttons are activated by a stylus or a similar tool. In preferred embodiments the push buttons have a top surface area in the range of 1 to 2 square millimeters. The push buttons are collectively referred to as the data input device. Note that the disposable cover 230 needs to be sufficiently robust to allow the data input device to be activated using a stylus, or similar tool, without perforation. The set of data buttons 212 includes: buttons with numbers 0 through 9 which can be used to identify tooth number, a measure of tooth mobility, a measure of tooth furcation or pocket depth; a "+" button used to increment the tooth number by 1; and a "−"button used to decrement the tooth number by 1. The "enter" button 213 is equivalent in function to the "enter" button on a conventional computer keyboard and is used to input data. The display 214 is a flat display, such as an LCD; the display can show either the tooth number for which data is being input or the data that is being input, thus providing feedback.

For example, at first the tooth number for which data is to be input is displayed, then, when data is input, the data itself is displayed—allowing the data input to be confirmed. The buttons 216 surrounding the display can be used to identify the side of the tooth—mesial, lingual, distal or buccal. The "erase" button 217 erases the previously entered number during data input. Note that the push buttons and display are oriented on the top surface of the head so as to be most easily viewed when the handle is upright (at twelve o'clock).

Figure 7:
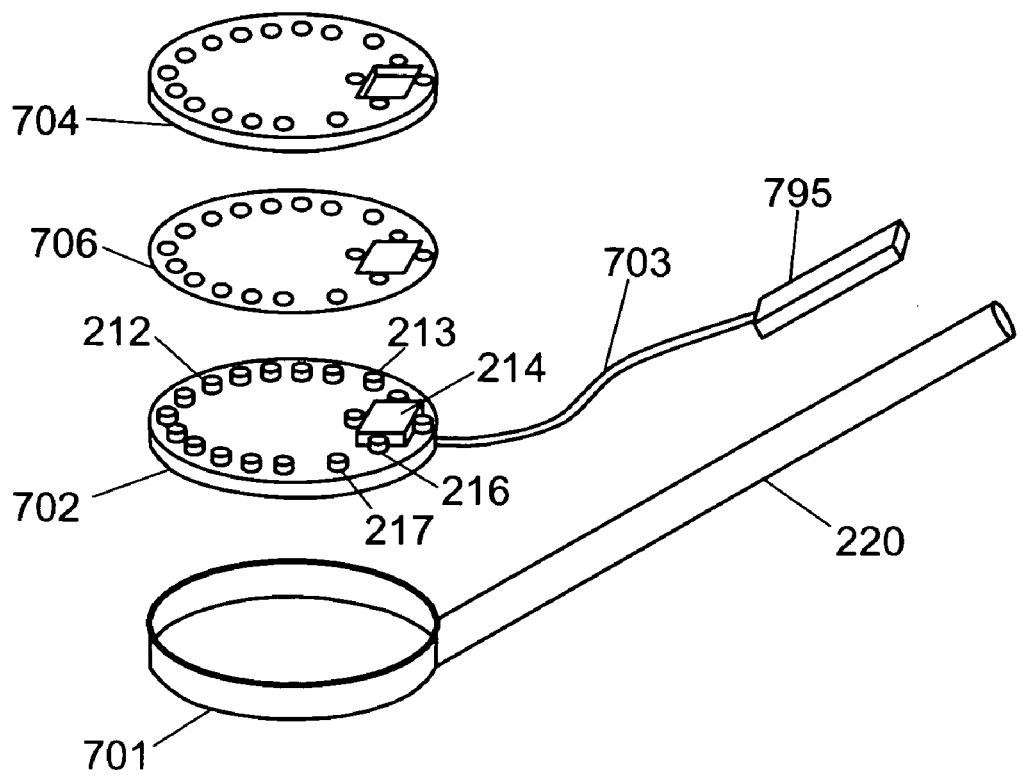
FIG. 7 is an exploded perspective view of the intraoral input device of FIG. 2.

The intraoral data input tool shown in FIGS. 2 & 3 can be linked to a controller 140 (see FIG. 1) by wireless communication. A wireless communication device can be contained within the handle, or the head, of the data input tool—an example is shown in FIG. 7. This embodiment of the intraoral data input device must have an internal power supply, such as a battery, which can be contained within the handle, or the head, of the data input tool. A rechargeable power supply is preferred and the data input tool can have external electrical contacts (not shown) for connection to a recharging device. Alternatively, an inductive recharging circuit, including a coil, can be contained within the data input tool; when not in use, the data input tool is recharged by placing it in a custom docking station.

Figure 9:
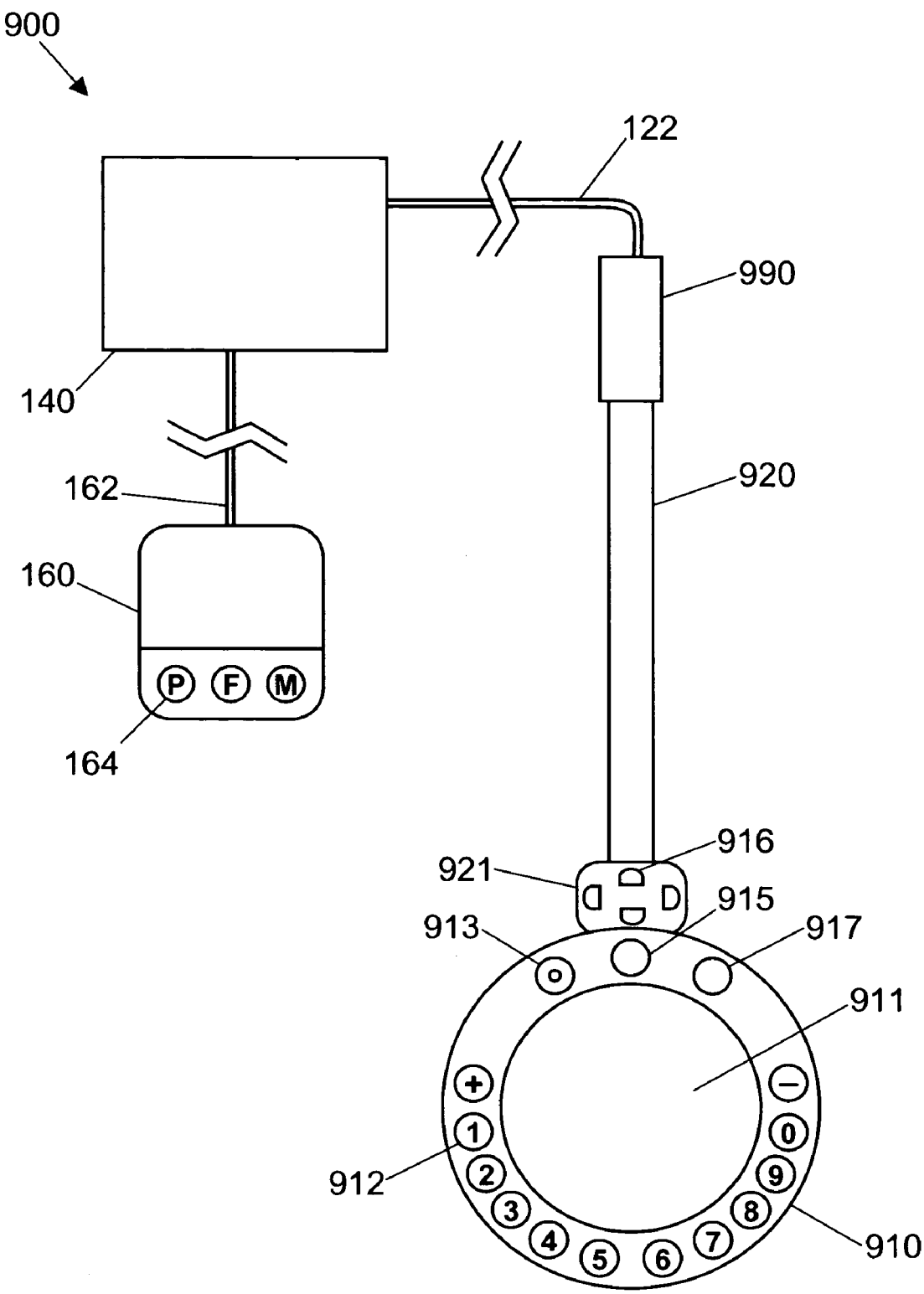
FIG. 9 is a schematic representation of a second embodiment of a dental data input system in accordance with the invention.

The intraoral data input tool shown in FIGS. 2 & 3 can be linked to an auxiliary input device 160 (see FIG. 1); the auxiliary input device can be configured to select a periodontal program—the buttons 164 can be labeled P, F, and M for probing, furcation and mobility, respectively (see FIG. 9).

With reference to the intraoral data input tool of FIG. 2, and assuming that the intraoral data input tool is linked to an auxiliary input device 160 configured for selection of a periodontal program (as shown in FIG. 9), some examples of data input sequences are given below. Other input sequences and variations of the input sequences given below will be apparent to those skilled in the art.

The first example is a tooth mobility data input sequence carried out by a dentist or hygienist.
1. Activate the "M" button on the auxiliary input device.
2. Examine the patient's teeth, looking for a mobile tooth.
3. When a mobile tooth is located, measure the mobility (1, 2 or 3).
4. Activate the "+" or "−" buttons on the intraoral data input tool until the desired tooth number is reached (tooth number is displayed on display 214).
5. Activate the appropriate numeric button 212 to enter the mobility value (1, 2 or 3); the mobility value is displayed on display 214.
6. Activate the "enter" button 213.
7. Repeat steps 2 through 6 as required.

Clearly, the input sequence can be varied in many ways. For example: step 6 may be dropped between measurements and only used after all mobility measurements have been input; the tooth number may be input directly using the numeric buttons on the intraoral data input tool. As an example of how to edit data input, the following sequence for correcting a mobility value is provided where it is assumed that the dentist or hygienist has completed steps 1 through 5 of the tooth mobility data input sequence given above.
5a. Activate the "erase" button 217.
5b. Activate the appropriate numeric button to enter the correct mobility value (1, 2 or 3).

The second example is a furcation data input sequence carried out by a dentist or hygienist.
1. Activate the "F" button on the auxiliary input device.
2. Examine and if necessary measure the furcation of a patient's tooth, starting with tooth number 1.
4. If a measurement needs to be recorded, then (a) activate the "+" or "−" buttons on the intraoral data input tool until the desired tooth number is reached (tooth number is displayed on display 214), (b) activate the appropriate button 216 to indicate the location of the measurement (M, L, B or D) (c) activate the appropriate numeric button 212 to enter the furcation value (1, 2 or 3), and repeat steps (b) and (c) until all desired measurements are recorded.
5. Activate the "enter" button.
6. Repeat steps 2 through 5 as required.

The third example is a periodontal probing data input sequence carried out by a dentist or hygienist, where a voice synthesizer 170 is Used (see FIG. 1).
1. Activate the "P" button on the auxiliary input device.
2. The voice synthesizer calls for measurements on tooth number X.
3. Take three measurements of the probing depth (1 through 9) on either the lingual or buccal side of tooth X using a graduated probe.
4. Input the three numeric values by sequentially activating appropriate numeric buttons 212.
5. The voice synthesizer calls out the input values.
6. If incorrect, then activate "erase" button 217, and return to step (4).
7. If correct, then activate "enter" button 213.
8. Repeat steps 2 through 7 for X=1, 2, . . . 16 for the buccal side, X=16, 15 . . . 1 for the lingual side, X=17, 18, . . . 32 for the buccal side and X=32, 31 . . . 17 for the lingual side.

Clearly, the input sequence can be varied in many ways. For example, if the patient is missing a tooth, then the dentist or hygienist can activate the "+" button between steps 2 and 3 to move to the next tooth in the sequence.

Figure 4:
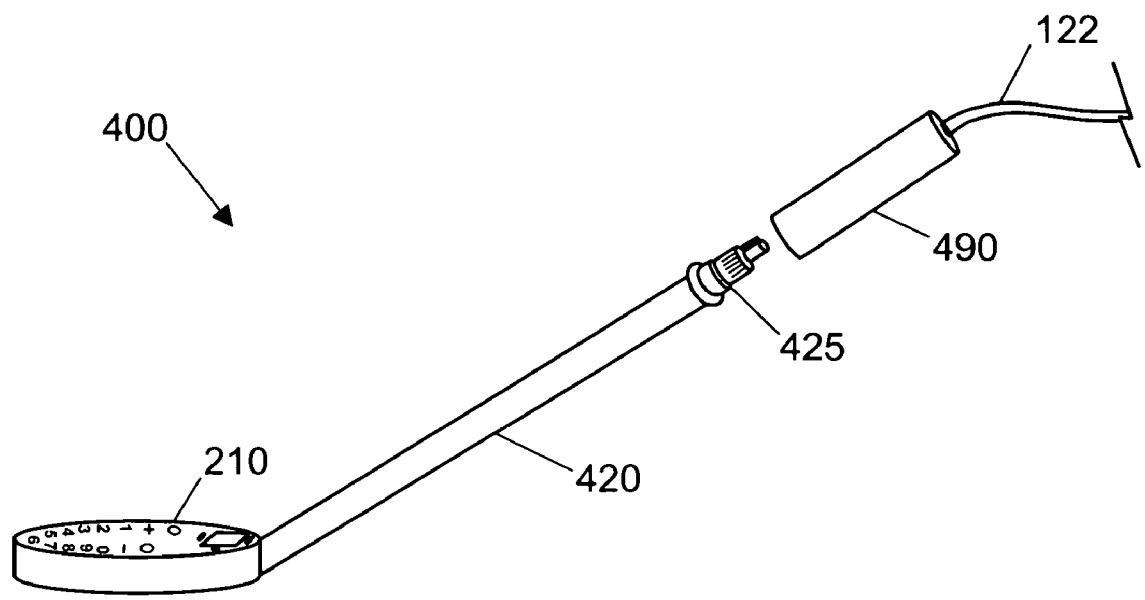
FIG. 4 is a perspective view of a second embodiment of an intraoral data input tool with an electrical connector in accordance with the invention.
Figure 5:
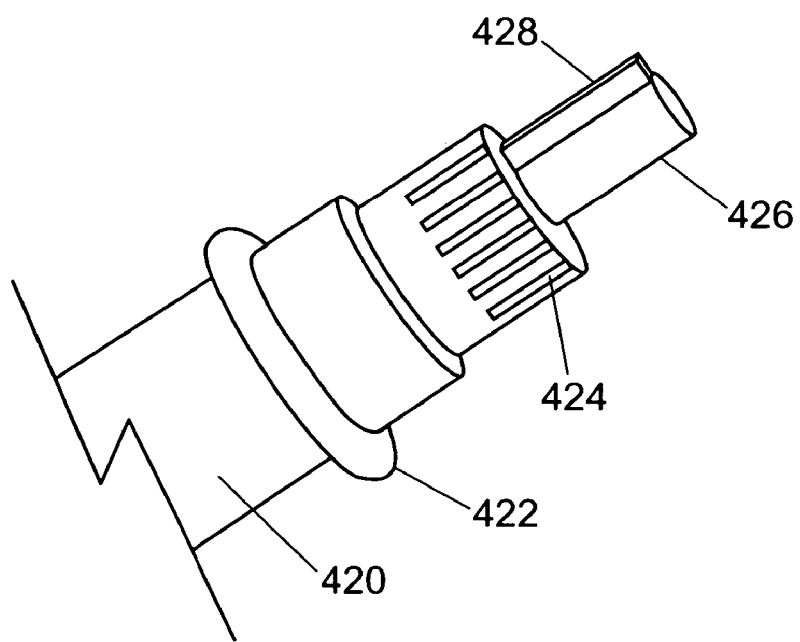
FIG. 5 is a detailed perspective view of the electrical connection at the end of the intraoral data input device of FIG. 4.

In FIGS. 4 & 5, a second embodiment of an intraoral data input tool 400 is shown. The intraoral data input tool has a head 210 attached to a handle 420. Electrical connectors 425 and 490 connect the intraoral data input tool to an electrical cable 122; FIG. 4 shows the connectors as a plug 425 and a socket 490. FIG. 5 shows an enlarged view of the electrical plug 425 on the end of the handle 420. There is an o-ring 422 situated on the handle, to ensure a snug fit with the socket 490. Electrical contacts 424 are aligned correctly to the socket 490 by the alignment key 428 situated on the guide 426. Other embodiments of the intraoral data input tool (not shown) have the configuration of the connectors reversed, such that the plug is attached to the electrical cable and the socket is attached to the end of the handle.

Figure 6:
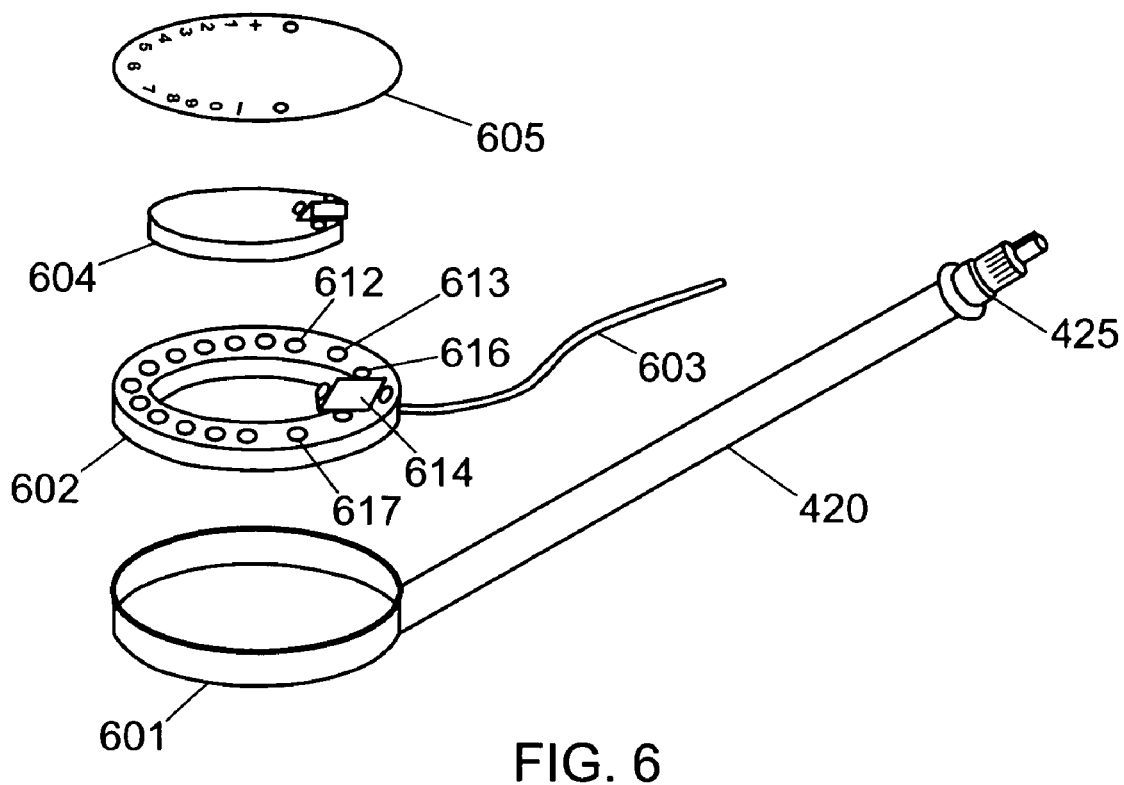
FIG. 6 is an exploded perspective view of the intraoral input device of FIG. 4.

With reference to FIG. 6, an exploded view of the intraoral data input tool of FIG. 4 is shown. The handle is shown with a rigid pan 601 on one end and the electrical connector 425 on the other end. A circuit board 602 fits within the pan; an electrical cable 603 connects the circuit board to the electrical connector 425. A set of twelve data push buttons 612, an 'enter' push button 613, a display 614, a set of four location identifying push buttons 616 surrounding the display and an 'erase' push button 617 are all attached to the circuit board. The configuration and function of the display and the push buttons is the same as described above for the intraoral data input device of FIG. 2. A mirror 604 fits within the circuit board 602. A flexible plastic cover 605 is sealed at its periphery to the rigid pan 601, providing a hermetic seal. The flexibility of the plastic cover 605 also allows the push buttons to be activated by pressure from a stylus or other suitable instrument.

FIG. 7 shows an exploded view of the intraoral data input tool of FIG. 2. The handle 220 is shown with a rigid pan 701 on the one end. A circuit board 702 fits within the pan; an electrical cable 703 connects the circuit board to a wireless communication device 795; the communication device can be housed within the handle 220. The set of twelve data push buttons 212, an 'enter' push button 213, a display 214, a set of four location identifying push buttons 216 surrounding the display and an 'erase' push button 217 are all attached to the circuit board. The configuration and function of the display and the buttons is the same as described above for the intraoral data input device of FIG. 2. A mirror 704, with apertures for the buttons and display, fits over the circuit board 702. A gasket 706 is placed between the circuit board 702 and the mirror 704, sealing all of the apertures in the mirror and sealing the mirror at its periphery to the rigid pan 701, providing a hermetic seal.

As described above with reference to FIG. 1, the intraoral data input tool is held by its handle in one hand and a stylus, or similar tool, is held in the other hand. When the dentist or hygienist inputs data on the head of the tool with the stylus, the intraoral data input tool must not exhibit any appreciable bending—the intraoral data input tool must be a rigid structure. The intraoral data input tool must also meet the standard requirements for a dental tool for use in a patient's mouth. The handle and head (420 and 601, respectively in FIG. 6; 220 and 701, respectively in FIG. 7) can be manufactured from materials such as stainless steel or suitable plastics. When a mirror is incorporated in the tool it must be made of medical grade, impact resistant glass. Furthermore, non-disposable embodiments of the intraoral data input tool must be constructed to be compatible with sterilization procedures.

Figure 8:
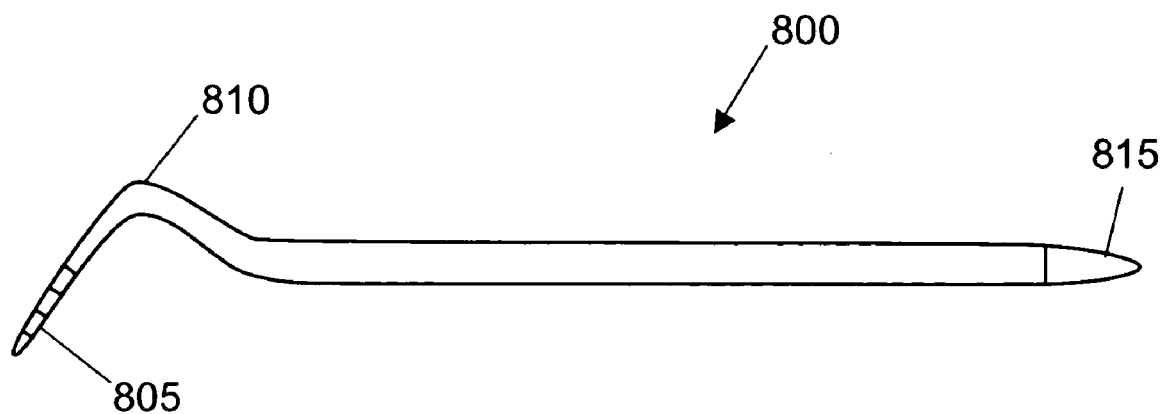
FIG. 8 is a side view of a probe in accordance with the invention.

In FIG. 8, a graduated probe 800 suitable for periodontal probing is shown. The probe has a graduated end 805 and the other end is configured as a stylus 815. Both the graduated end and the stylus can be used for data input on the intraoral data input tool. A knee 810 on the probe can also be used for data input. A graduated probe is commonly made of plastic.

With reference to FIG. 9, a second embodiment of a dental data input system 900 is shown. An intraoral data input tool is shown including an electrical connector 990, a handle 920 and a head 910. Where the handle is attached to the head, there is a surface 921 which includes a set of four location identifying push buttons 916. The top surface of the head 910 is shown to include: a mirror 911, a set of twelve data push buttons 912, an 'enter' push button 913, a 'home' push button 915 and an 'erase' push button 917. The function of the buttons is the same as described above for the intraoral data input device of FIG. 2. This configuration is for a periodontal tool. The push buttons can be pressure pads or another type of pressure activated switch. The intraoral data input tool is connected to controller 140 by electrical cable 122. Auxiliary input device 160 is connected to the controller by electrical cable 162. The auxiliary input device 160 has keys 164, which are used to select the periodontal program—the keys are labeled P, F, and M for probing, furcation and mobility, respectively; these keys can be operated by finger, stylus, or other convenient tool. Alternatively, the keys can be replaced by pressure pads, thus providing an auxiliary input device which is easier to clean. Various other peripheral devices can be connected to the controller 140. For example, a display screen, a keyboard and a voice synthesizer can be connected to the controller.

In the dental data input systems shown in FIGS. 1 & 9 the auxiliary input device is placed within immediate reach of the dentist or hygienist (from the position in which he/she conducts a dental examination of a patient). This configuration can be used to put a greater number of input options within immediate reach of the dentist or hygienist; alternatively, it can be used to reduce the number of input buttons on the intraoral data input device.

Figure 10:
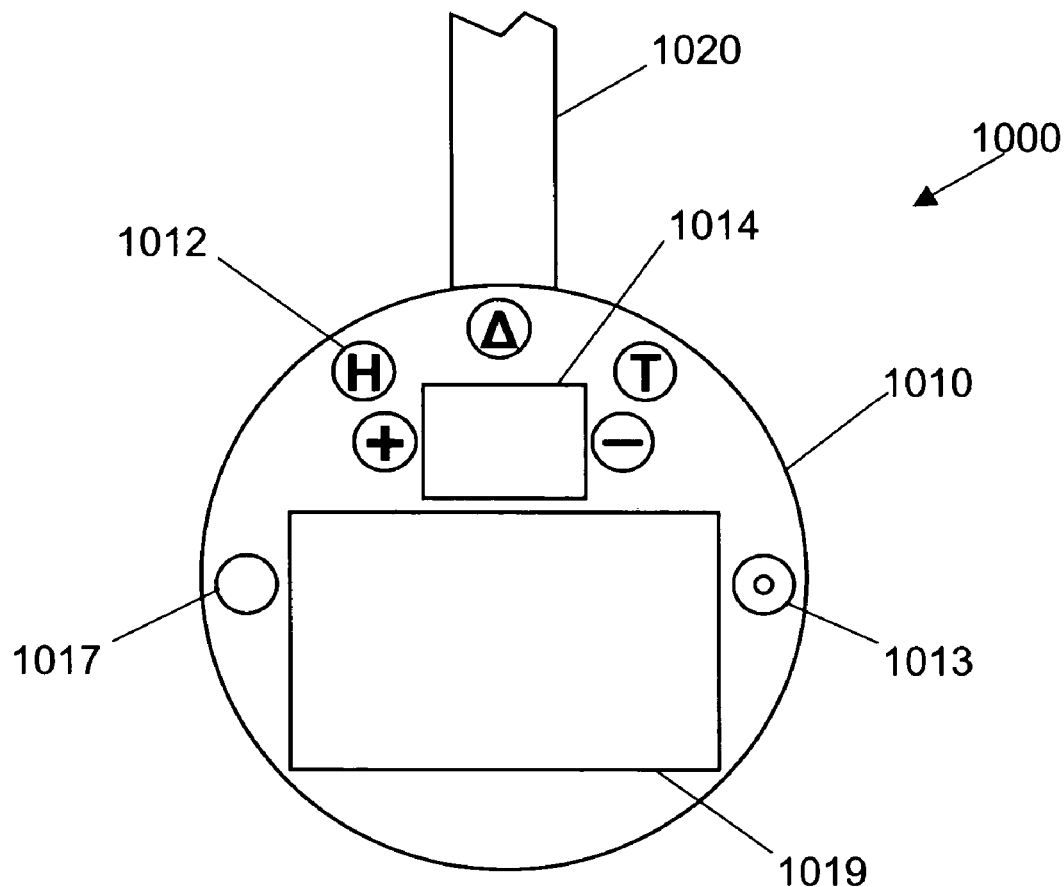
FIG. 10 is a top view of a third embodiment of an intraoral data input tool in accordance with the invention.

In FIG. 10, a third embodiment of an intraoral data input tool 1000 is shown. In order to clearly show the head 1010, most of the handle 1020 is not shown. The top surface of the head 1010 is shown to include: a set of five data push buttons 1012, an 'enter' push button 1013, an 'erase' push button 1017, a display 1014 and a touch sensitive display 1019. This top surface configuration is for a historic/diagnostic/treatment charting tool. The combination of push buttons and touch sensitive display is another embodiment of the data input device. The 'enter' button is equivalent in function to the 'enter' button on a conventional computer keyboard and is used to input data. The 'erase' button erases the previously entered number during data input. The set of data buttons 1012 includes a '+' button used to increment the tooth number by 1; and a '−' button used to decrement the tooth number by 1. The remaining data buttons designate the type of data input; specifically: H, historic; Δ, diagnostic; and T, treatment. The buttons can be pressure pads or another type of pressure activated switch. The display 1014 can show either the tooth number for which data is being input or the data that is being input, thus providing feedback. The touch sensitive display 1019 is responsive to force applied by a stylus, or a similar tool, and is used for the input of data such as: tooth number, type of tooth restoration, type of dental prosthesis or type of dental extraction. As is well know in the art of palm computers with touch sensitive displays, the user can set-up his/her own shorthand for data entry; consequently, the dentist or hygienist can enter data by writing in shorthand with a stylus on the touch sensitive display. Alternatively, the touch sensitive display 1019 can be set-up to display entry boxes, appropriate to the type of data input, for the dentist or hygienist to select using a stylus or similar tool. Data may conveniently be input and displayed using a code. For example, the code CO1A might be used to signify a resin base composite on the surface of one anterior tooth.

With reference to the intraoral data input tool of FIG. 10, some examples of data input sequences are given below. Other input sequences and variations of the input sequences given below will be apparent to those skilled in the art.

The first example is a historic data input sequence carried out by a dentist or hygienist.

The first example is a historic data input sequence carried out by a dentist or hygienist.

1. Activate the "H" button on the intraoral data input tool.
2. Examine the patient's teeth, looking for restorative work.
3. When a restoration is found activate the "+" or "−" buttons until the desired tooth number is reached (tooth number is displayed on display 1014).
4. Write/input the shorthand for the restoration on touch sensitive display 1019; the code for the restoration is displayed on display 1019.
5. Activate the "enter" button 1013.
6. Repeat steps 4 and 5 as required, for further restoration on the same tooth.
7. Repeat steps 2 through 6 as required until all teeth have been examined. Note that the examination will often start with tooth number 1. Clearly, the above input sequence can be varied in many ways. For example: in step 4 instead of the code being displayed on the touch sensitive display it may be called out by a voice synthesizer. As an example of how to edit data input, the following sequence for correcting a restoration code is provided where it is assumed that the dentist or hygienist has completed steps 1 through 4 of the historic data input sequence given above.

4a. Activate the "erase" button 1017.

4b. Write/input the shorthand for the correct restoration on touch sensitive display 1019; the corrected code is displayed on display 1019.

The second example is a diagnostic data input sequence carried out by a dentist or hygienist.

1. Activate the "Δ" button on the intraoral data input tool.
2. Examine the patient's teeth, looking for problems.
3. When a problem is found activate the "+" or "−" buttons until the desired tooth number is reached (tooth number is displayed on display 1014).
4. Write/input the shorthand for the problem on touch sensitive display 1019; the code for the problem is displayed on touch sensitive display 1019.
5. Activate the "enter" button 1013.
6. Repeat steps 4 and 5 as required, for further problems on the same tooth.
7. Repeat steps 2 through 6 as required until all teeth have been examined.

The third example is a treatment data input sequence carried out by a dentist or hygienist 1. Activate the "T" button on the intraoral data input tool.
2. Examine the patient's teeth, looking for work that needs to be done.
3. When a tooth requiring work is found activate the "+" or "−" buttons until the desired tooth number is reached (tooth number is displayed on display 1014).
4. Write/input the shorthand for the treatment on touch sensitive display 1019; the code for the treatment is displayed on touch sensitive display 1019.
5. Activate the "enter" button 1013.
6. Repeat steps 4 and 5 as required, for further work needed on the same tooth.
7. Repeat steps 2 through 6 as required until all teeth have been examined.

The intraoral data input tool 1000 of FIG. 10 can be used in the dental data input system shown in FIG. 1; this data input tool can be linked to a controller by either an electrical cable or a wireless communication device, as described above.

When codes are used to enter and/or display data using the intraoral data input tool of FIG. 10, it may be easiest for the dentist or hygienist to develop his/her own code—a code which is easy to remember. The American Dental Association has established standard codes (CDT4) for general use by dentists, dental insurance companies, etc.; however, these codes may be more difficult to remember. As a convenience, the controller that is used in conjunction with the intraoral data input tool can be programmed with a look-up table providing insurance codes corresponding to the dentist's own codes; this will assist the dentist or hygienist in the preparation of insurance claims. Clearly, the controller can be linked to other computers and peripherals, particularly those that are used to prepare insurance claims and similar documents.

Figure 11:
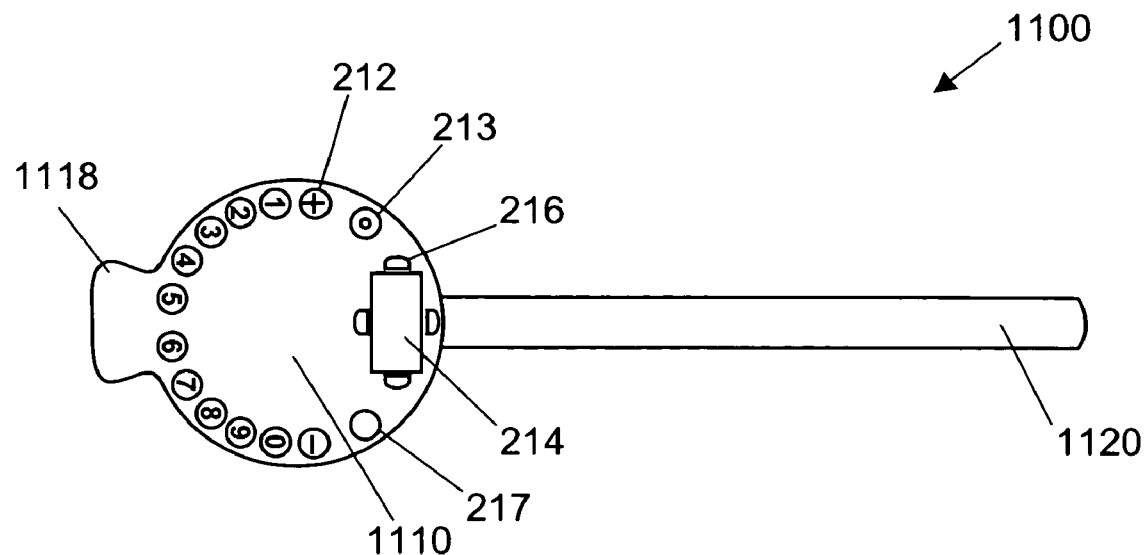
FIG. 11 is a top view of a fourth embodiment of an intraoral data input tool with an extrusion attached to the head of the tool.
Figure 12:
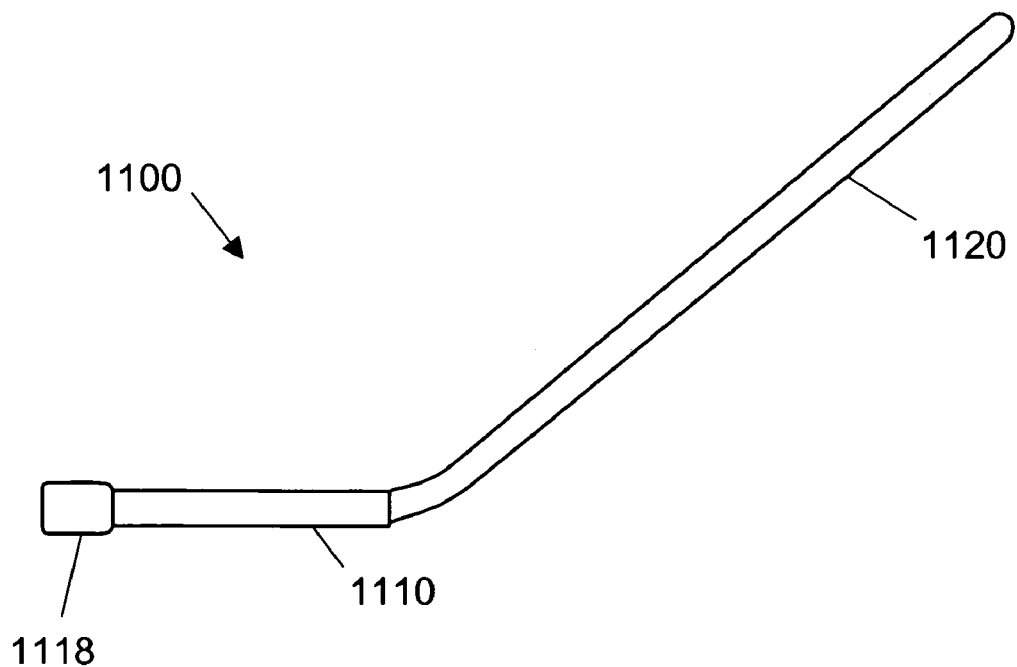
FIG. 12 is a side view of the intraoral data input tool of FIG. 11.

With reference to FIGS. 11 & 12, two views of a fourth embodiment of an intraoral data input tool 1100 are shown. The intraoral data input tool has a discoid head 1110 attached to a handle 1120. An extrusion 1118 is attached to the head 1110; the extrusion is positioned on the perimeter of the discoid head diametrically opposite from the handle; the extrusion extends approximately radially from the discoid head. The top surface of the head 1110 is shown with a set of twelve data push buttons 212, an 'enter' push button 213, a display 214, a set of four location identifying push buttons 216 surrounding the display and an 'erase' push button 217. This top surface configuration is the same as for FIG. 2 and has been described above—see the detailed description of FIG. 2. The intraoral data input tool is typically held in the left hand, gripped between the thumb and first (index) and second fingers; for stability, the other fingers of the left hand can be positioned on the patient's teeth (in a position which does not cause any discomfort). The stylus is typically held in the right hand, gripped between the thumb and first (index) finger. In order to provide extra stability while inputting data with the stylus, either the third or fourth finger of the right hand can be rested either on top of or against the side of the extrusion 1118.

In some embodiments of the intraoral data input tool with a touch sensitive display, the touch sensitive display has a mirror-like surface—providing the best functional compromise of a mirror and a flat display. Furthermore, in some embodiments the touch sensitive display: covers most of the top surface of the head of the intraoral data input tool; and is the only means for data input and display on the intraoral data input tool.

Embodiments of the intraoral data input tool such as that shown in FIG. 10 can benefit from having a mirror on the lower surface of the head (on the opposite side of the discoid head to the data input device). When a mirror is incorporated on the lower surface of the head, the angle between the handle and a diameter of the discoid head is adjusted from that shown in FIGS. 3, 4, 6 & 7 to nearly 180 degrees; this configuration of the head relative to the handle is similar to that of a double sided dental mirror.

Some embodiments of the intraoral data input tool are designed for single use (i.e. disposable). Clearly, these tools will need to be sufficiently inexpensive to manufacture to be widely used as disposables; such a tool will probably have push buttons surrounding a mirror (without a display), a handle and head made of plastic, and an electrical connector on the end of the handle (similar to the connector shown in FIG. 5).

The data input device of this invention has been described as being incorporated into a tool which is similar in size and shape to a standard dental mirror. However, the data input device can be incorporated into any support structure that enables the dentist or hygienist to conveniently use the device for data input in or near the patient's mouth. The term 'near the patient's mouth' is best defined as any position which allows the dentist or hygienist to maintain his/her visual focus, as required for examination of the patient's teeth; thus reducing eye fatigue due to repeatedly changing visual focus.

The foregoing description of various embodiments of the invention has been presented for purposes of illustration and description. It is not intended to limit the invention to the precise forms disclosed. Many modifications and equivalent arrangements will be apparent.

What is claimed is:

1. A dental data input system comprising:
   an intraoral data input tool including:
      a rigid pan having a bottom surface and a side wall around the periphery of said bottom surface;
      a handle rigidly attached to said side wall of said pan;
      a circuit board positioned within said pan, said circuit board including a data input device;

a mirror positioned centrally within said pan;
a cover positioned over said circuit board, said cover being configured to hermetically seal said circuit board within said pan; and
a stylus;
wherein said data input device is responsive to force applied by said stylus, and said intraoral data input tool is configured to allow a dental examiner to input data using said stylus on said data input device when said data input device is comfortably positioned at least partially within a patient's mouth.

2. A dental data input system as in claim 1 wherein said stylus is a dental probe.

3. A dental data input system as in claim 2 wherein said stylus includes a graduated end for periodontal probing.

4. A dental data input system as in claim 3 wherein said stylus includes a knee adjacent to said graduated end, said stylus being configured to allow data input with said knee.

5. A dental data input system as in claim 2 wherein said stylus includes a graduated end configured for periodontal probing and a second end configured for use in data input.

6. A dental data input system as in claim 1 further comprising a controller with an operating program, said controller being linked to said intraoral data input tool by a communication means.

7. A dental data input system as in claim 6 wherein said communication means comprises an electrical cable.

8. A dental data input system as in claim 6 wherein said communication means is a wireless communication means.

9. A dental data input system as in claim 6 wherein said operating program includes a routine for periodontal examination.

10. A dental data input system as in claim 6 wherein said operating program includes a routine for dental charting.

11. A dental data input system as in claim 6 further comprising:
a display electrically connected to said controller; and
a keyboard electrically connected to said controller.

12. A dental data input system as in claim 6 further comprising a voice synthesizer electrically connected to said controller.

13. A dental data input system as in claim 6 further comprising an auxiliary input device electrically connected to said controller.

14. An intraoral data input tool for use during dental examination of a patient, said tool comprising:
a rigid pan having a bottom surface and a side wall around the periphery of said bottom surface;
a handle rigidly attached to said side wall of said pan;
a circuit board positioned within said pan, said circuit board including push buttons and a display;
a mirror positioned centrally within said pan; and
a cover positioned over said circuit board, said cover being configured to hermetically seal said circuit board within said pan;
wherein said push buttons are responsive to force applied by a stylus, and wherein said intraoral data input tool is configured to allow a dental examiner to input data using said stylus when said pan is comfortably positioned at least partially within said patient's mouth.

15. The intraoral data input tool of claim 14 further comprising a platform with push buttons, said platform being rigidly attached to said tool at the position where said handle is attached to said side wall of said pan.

16. The intraoral data input tool of claim 14 wherein said circuit board has a central cutout, said mirror is positioned within said central cutout of said circuit board, said cover is positioned over said mirror and said circuit board, and said cover is configured to hermetically seal said circuit board and said mirror within said pan.

17. The intraoral data input tool of claim 14 wherein said mirror is positioned over said circuit board and said mirror has apertures for said push buttons and said display, said cover is a gasket positioned between said circuit board and said mirror, said gasket hermetically sealing all of said apertures in said mirror and hermetically sealing said mirror to the periphery of said pan.

18. An intraoral data input tool of claim 14 wherein said handle is generally cylindrical, the diameter of said handle being much smaller than the length of said handle.

19. An intraoral data input tool of claim 14 wherein said rigid pan is discoid.

20. An intraoral data input tool of claim 19 wherein said discoid rigid pan has a diameter of approximately 2.5 centimeters.

21. The intraoral data input tool of claim 14 further comprising an extrusion rigidly attached to the perimeter of said rigid pan, positioned diametrically opposite to said handle, said extrusion extending radially from said rigid pan, said extrusion being configured to allow said dental examiner to place one or more fingers of said examiner's stylus bearing hand against said extrusion to provide extra stability when inputting data with said stylus.

22. The intraoral data input tool of claim 14 wherein each of said push buttons has a top surface area in the range of 1 to 2 square millimeters.

23. The intraoral data input tool of claim 14 wherein said circuit board further includes a touch sensitive display.

24. The intraoral data input tool of claim 14 wherein said push buttons are located peripherally about said mirror.

25. The intraoral data input tool of claim 14 wherein said display is a touch sensitive display.

26. The intraoral data input tool of claim 14 further comprising a translucent disposable cover.

27. The intraoral data input tool of claim 26 further comprising a clamp configured to keep said disposable cover conformal with the surface of said mirror.

28. The intraoral data input tool of claim 27 wherein said damp is a c-clamp and said rigid pan is discoid with a concave side wall, said concave side wall retaining said c-clamp.

29. The intraoral data input tool of claim 14 further comprising a wireless communication device contained within said handle, said communication device being electrically connected to said circuit board.

30. The intraoral data input tool of claim 14 further comprising:
an electrical connector attached to the opposite end of said handle from said rigid pan; and
an electrical cable connecting said electrical connector to said circuit board.

31. The intraoral data input tool of claim 14 wherein said stylus is a dental probe.

32. The intraoral data input tool of claim 14 wherein the length of said handle is approximately 13 centimeters.

33. The intraoral data input tool of claim 14 wherein the diameter of said handle is smaller than the length of said handle, the rigid pan is discoid and has a flat bottom surface, and the long axis of said handle is in a plane containing a diameter of said discoid pan.

34. The intraoral data input tool of claim 33 wherein said plane is perpendicular to said flat bottom surface of said rigid pan.

35. An intraoral data input tool for use during dental examination of a patient, said tool comprising:
- a rigid pan having a bottom surface and a side wall around the periphery of said bottom surface;
- a handle rigidly attached to said side wall of said pan;
- a circuit board positioned within said pan, said circuit board including push buttons, a display, and a touch sensitive display; and
- a cover positioned over said circuit board, said cover being configured to hermetically seal said circuit board within said pan;
- wherein said push buttons and said touch sensitive display are responsive to force applied by a stylus, and wherein said intraoral data input tool is configured to allow a dental examiner to input data using said stylus when said pan is comfortably positioned at least partially within said patient's mouth.

36. The intraoral data input tool of claim 35 wherein said bottom surface of said rigid pan includes a mirror.

37. The intraoral data input tool of claim 36 wherein the diameter of said handle is smaller than the length of said handle, the rigid pan is discoid and has a flat bottom surface, and the long axis of said handle is in a plane parallel to the plane containing the flat bottom surface of said discoid pan.

38. The intraoral data input tool of claim 5 wherein the diameter of said handle is smaller than the length of said handle, the rigid pan is discoid and has a flat bottom surface, and the long axis of said handle is in a plane containing a diameter of said discoid pan.

39. The intraoral data input tool of claim 35 wherein said touch sensitive display covers most of the top surface of the head of said intraoral data input tool.

40. The intraoral data input tool of claim 39 wherein said touch sensitive display has a mirror-like surface.

* * * * *